(12) United States Patent
Vitello (10) Patent No.: US 12,070,591 B1
(45) Date of Patent: Aug. 27, 2024

(54) SNAP ACTION TAMPER EVIDENT CLOSURE ASSEMBLY

(71) Applicant: Patrick Vitello, Pompano Beach, FL (US)

(72) Inventor: Patrick Vitello, Pompano Beach, FL (US)

(*) Notice: Subject to any disclaimer, the term of this patent is extended or adjusted under 35 U.S.C. 154(b) by 0 days.

(21) Appl. No.: 17/551,002

(22) Filed: Dec. 14, 2021

Related U.S. Application Data (60) Provisional application No. 63/125,156, filed on Dec. 14, 2020.

(51) Int. Cl.
*A61M 5/50* (2006.01)
*B65D 55/02* (2006.01)

(52) U.S. Cl.
CPC .......... *A61M 5/5086* (2013.01); *B65D 55/026* (2013.01)

(58) Field of Classification Search
CPC .............. A61M 5/3202; A61M 5/5086; A61M 39/1011; B65D 43/0237; B65D 43/0204; B65D 55/026
See application file for complete search history.

(56) References Cited

U.S. PATENT DOCUMENTS

| | | |
|---|---|---|
| 722,943 A | 3/1903 | Chappell |
| 732,662 A | 6/1903 | Smith |
| 1,678,991 A | 7/1928 | Marschalek |
| 1,970,631 A | 8/1934 | Sherman |
| 2,477,598 A | 8/1949 | Hain |
| 2,739,590 A | 3/1956 | Yochem |
| 2,823,674 A | 2/1958 | Yochem |
| 2,834,346 A | 5/1958 | Adams |
| 2,875,761 A | 3/1959 | Helmer et al. |
| 2,888,015 A | 5/1959 | Hunt |
| 2,952,255 A | 9/1960 | Hein, Jr. |

(Continued)

FOREIGN PATENT DOCUMENTS

| | | |
|---|---|---|
| DE | 202008018507 | 2/2015 |
| EP | 0148116 | 7/1985 |

(Continued)

OTHER PUBLICATIONS

Arai Tsugio, Pilfering Proof Cap, Jan. 1, 1996.

*Primary Examiner* — Andrew T Kirsch
(74) *Attorney, Agent, or Firm* — Malloy & Malloy, P.L.; Jennie S. Malloy (57) ABSTRACT

A tamper evident closure (TEC) for a medical container includes a cover having an access opening and a tip cap removably disposed therein. First and second snap structures are respectively disposed within said cover and on said tip cap and are cooperatively disposed and configured to removably restrict exiting of said tip cap from said cover, via said access opening and in movable engagement with one another concurrent to said exiting of said tip cap. Each of the first and second snap structures are disposed and configured for movable, sliding engagement with one another, concurrent to the exiting of said tip cap. At least one component of the TEC is dimensioned and configured to define a flexure thereof, concurrent to the sliding engagement of first and second snap structures, resulting in a snap-action disconnection of said tip cap from said cover.

14 Claims, 3 Drawing Sheets

(56) References Cited

U.S. PATENT DOCUMENTS

| | | |
|---|---|---|
| 3,122,280 A | 2/1964 | Goda |
| 3,245,567 A | 4/1966 | Knight |
| 3,323,798 A | 6/1967 | Miller |
| 3,364,890 A | 1/1968 | Andersen |
| 3,368,673 A | 2/1968 | Johnson |
| 3,489,268 A | 1/1970 | Meierhoefer |
| 3,574,306 A | 4/1971 | Alden |
| 3,598,120 A | 8/1971 | Mass |
| 3,610,241 A | 10/1971 | LeMarie |
| 3,674,181 A | 7/1972 | Marks et al. |
| 3,700,215 A | 10/1972 | Hardman et al. |
| 3,706,307 A | 12/1972 | Hasson |
| 3,712,749 A | 1/1973 | Roberts |
| 3,726,445 A | 4/1973 | Ostrowsky et al. |
| 3,747,751 A | 7/1973 | Miller et al. |
| 3,850,329 A | 11/1974 | Robinson |
| 3,872,867 A | 3/1975 | Killinger |
| 3,904,033 A | 9/1975 | Haerr |
| 3,905,375 A | 9/1975 | Toyama |
| 3,937,211 A | 2/1976 | Merten |
| 3,987,930 A | 10/1976 | Fuson |
| 4,005,739 A | 2/1977 | Winchell |
| 4,043,334 A | 8/1977 | Brown et al. |
| 4,046,145 A | 9/1977 | Choksi et al. |
| 4,068,696 A | 1/1978 | Winchell |
| 4,106,621 A | 8/1978 | Sorenson |
| 4,216,585 A | 8/1980 | Hatter |
| 4,216,872 A | 8/1980 | Bean |
| 4,244,366 A | 1/1981 | Raines |
| 4,252,122 A | 2/1981 | Halvorsen |
| 4,271,972 A | 6/1981 | Thor |
| 4,286,591 A | 9/1981 | Raines |
| 4,286,640 A | 9/1981 | Knox et al. |
| 4,313,539 A | 2/1982 | Raines |
| 4,369,781 A | 1/1983 | Gilson et al. |
| 4,420,085 A | 12/1983 | Wilson et al. |
| 4,430,077 A | 2/1984 | Mittleman et al. |
| 4,457,445 A | 7/1984 | Hanks et al. |
| 4,482,071 A | 11/1984 | Ishiwatari |
| D277,783 S | 2/1985 | Beck |
| 4,521,237 A | 6/1985 | Logothetis |
| 4,530,697 A | 7/1985 | Kuhlemann et al. |
| 4,571,242 A | 2/1986 | Klien et al. |
| 4,589,171 A | 5/1986 | McGill |
| 4,664,259 A | 5/1987 | Landis |
| 4,667,837 A | 5/1987 | Vitello et al. |
| 4,676,530 A | 6/1987 | Nordgren et al. |
| 4,693,707 A | 9/1987 | Dye |
| 4,726,483 A | 2/1988 | Drozd |
| 4,735,617 A | 4/1988 | Nelson et al. |
| 4,742,910 A | 5/1988 | Staebler |
| 4,743,229 A | 5/1988 | Chu |
| 4,743,231 A | 5/1988 | Kay et al. |
| 4,760,847 A | 8/1988 | Vaillancourt |
| 4,813,564 A | 3/1989 | Cooper et al. |
| 4,832,695 A | 5/1989 | Rosenberg et al. |
| 4,834,706 A | 5/1989 | Beck et al. |
| 4,842,592 A | 6/1989 | Caggiani et al. |
| 4,844,906 A | 7/1989 | Hermelin et al. |
| 4,906,231 A | 3/1990 | Young |
| 4,919,285 A | 4/1990 | Roof et al. |
| 4,936,445 A | 6/1990 | Grabenkort |
| 5,009,323 A | 4/1991 | Montgomery et al. |
| 5,024,323 A | 6/1991 | Bolton |
| 5,049,129 A | 9/1991 | Zdeb et al. |
| D323,392 S | 1/1992 | Bryne |
| 5,078,696 A | 1/1992 | Nedbaluk |
| 5,085,332 A | 2/1992 | Gettig et al. |
| 5,090,564 A | 2/1992 | Chimienti |
| 5,133,454 A | 7/1992 | Hammer |
| 5,135,496 A | 8/1992 | Vetter et al. |
| 5,163,922 A | 11/1992 | McElveen, Jr. et al. |
| 5,165,560 A | 11/1992 | Ennis, III et al. |
| 5,230,429 A | 7/1993 | Etheredge, III |
| 5,267,983 A | 12/1993 | Oilschlager et al. |
| 5,292,308 A | 3/1994 | Ryan |
| 5,293,993 A | 3/1994 | Yates, Jr. et al. |
| 5,295,599 A | 3/1994 | Smith |
| 5,312,367 A | 5/1994 | Nathan |
| 5,312,368 A | 5/1994 | Haynes |
| 5,328,466 A | 7/1994 | Denmark |
| 5,328,474 A | 7/1994 | Raines |
| 5,356,380 A | 10/1994 | Hoekwater et al. |
| 5,370,226 A | 12/1994 | Gollobin et al. |
| 5,380,295 A | 1/1995 | Vacca |
| 5,402,887 A | 4/1995 | Shillington |
| 5,405,339 A | 4/1995 | Kohnen et al. |
| 5,456,668 A | 10/1995 | Ogle, II |
| 5,458,580 A | 10/1995 | Hajishoreh |
| 5,468,224 A | 11/1995 | Souryal |
| 5,474,178 A | 12/1995 | DiViesti et al. |
| 5,505,705 A | 4/1996 | Galpin et al. |
| 5,531,695 A | 7/1996 | Swisher |
| 5,540,324 A | 7/1996 | Knapp |
| 5,540,666 A | 7/1996 | Barta et al. |
| 5,549,571 A | 8/1996 | Sak |
| 5,558,648 A | 9/1996 | Shields |
| 5,584,817 A | 12/1996 | van den Haak |
| 5,588,239 A | 12/1996 | Anderson |
| 5,617,954 A | 4/1997 | Kato et al. |
| 5,624,402 A | 4/1997 | Imbert |
| 5,662,233 A | 9/1997 | Reid |
| 5,674,209 A | 10/1997 | Yarger |
| 5,695,470 A | 12/1997 | Roussigne et al. |
| 5,699,913 A | 12/1997 | Richardson |
| 5,700,247 A | 12/1997 | Grimard et al. |
| 5,702,374 A | 12/1997 | Johnson |
| 5,713,485 A | 2/1998 | Liff et al. |
| 5,776,124 A | 7/1998 | Wald |
| 5,785,691 A | 7/1998 | Vetter et al. |
| 5,797,885 A | 8/1998 | Rubin |
| 5,807,343 A | 9/1998 | Tucker et al. |
| 5,829,589 A | 11/1998 | Nguyen et al. |
| D402,766 S | 12/1998 | Smith et al. |
| 5,842,567 A | 12/1998 | Rowe et al. |
| 5,876,381 A | 3/1999 | Pond et al. |
| 5,883,806 A | 3/1999 | Meador et al. |
| 5,884,457 A | 3/1999 | Ortiz et al. |
| 5,902,269 A | 5/1999 | Jentzen |
| 5,926,922 A | 7/1999 | Stottle |
| 5,951,522 A | 9/1999 | Rosato et al. |
| 5,951,525 A | 9/1999 | Thorne et al. |
| 5,954,203 A | 9/1999 | Marconi |
| 5,954,657 A | 9/1999 | Rados |
| 5,957,166 A | 9/1999 | Safabash |
| 5,957,314 A | 9/1999 | Nishida et al. |
| 5,963,136 A | 10/1999 | O'Brien |
| 5,989,227 A | 11/1999 | Vetter et al. |
| 5,993,437 A | 11/1999 | Raoz |
| 6,000,548 A | 12/1999 | Tsals |
| D419,671 S | 1/2000 | Jansen |
| 6,021,824 A | 2/2000 | Larsen et al. |
| 6,027,482 A | 2/2000 | Imbert |
| 6,068,614 A | 5/2000 | Kimber et al. |
| D430,293 S | 8/2000 | Jansen |
| D431,864 S | 10/2000 | Jansen |
| 6,126,640 A | 10/2000 | Tucker et al. |
| 6,190,364 B1 | 2/2001 | Imbert |
| 6,193,688 B1 | 2/2001 | Balestracci et al. |
| 6,196,593 B1 | 3/2001 | Petrick et al. |
| 6,196,998 B1 | 3/2001 | Jansen et al. |
| 6,216,885 B1 | 4/2001 | Guillaume |
| 6,279,746 B1 | 4/2001 | Hussaini et al. |
| 6,235,376 B1 | 5/2001 | Miyazaki et al. |
| 6,280,418 B1 | 8/2001 | Reinhard et al. |
| 6,287,671 B1 | 9/2001 | Bright et al. |
| 6,322,543 B1 | 11/2001 | Singh et al. |
| 6,338,200 B1 | 1/2002 | Baxa et al. |
| 6,358,241 B1 | 3/2002 | Shapeton et al. |
| 6,375,640 B1 | 4/2002 | Teraoka |
| 6,394,983 B1 | 5/2002 | Mayoral et al. |
| 6,439,276 B1 | 8/2002 | Wood et al. |
| 6,485,460 B2 | 11/2002 | Eakins et al. |
| 6,488,666 B1 | 12/2002 | Geist |

(56) References Cited

U.S. PATENT DOCUMENTS

| | | |
|---|---|---|
| 6,491,665 B1 | 12/2002 | Vetter et al. |
| 6,500,155 B2 | 12/2002 | Sasso |
| 6,520,935 B1 | 2/2003 | Jansen et al. |
| 6,540,697 B2 | 4/2003 | Chen |
| 6,565,529 B1 | 5/2003 | Kimber et al. |
| 6,581,792 B1 | 6/2003 | Limanjaya |
| 6,585,691 B1 | 7/2003 | Vitello |
| 6,592,251 B2 | 7/2003 | Edwards et al. |
| 6,666,852 B2 | 12/2003 | Niedospial, Jr. |
| 6,682,798 B1 | 1/2004 | Kiraly |
| 6,726,652 B2 | 4/2004 | Eakins et al. |
| 6,726,672 B1 | 4/2004 | Hanly et al. |
| 6,764,469 B2 | 7/2004 | Broselow |
| 6,796,586 B2 | 9/2004 | Werth |
| 6,821,268 B2 | 11/2004 | Balestracci |
| D501,549 S | 2/2005 | McAllister et al. |
| 6,921,383 B2 | 7/2005 | Vitello |
| 6,935,560 B2 | 8/2005 | Andreasson et al. |
| 6,942,643 B2 | 9/2005 | Eakins et al. |
| 7,036,661 B2 | 5/2006 | Anthony et al. |
| 7,055,273 B2 | 6/2006 | Roshkoff |
| 7,100,771 B2 | 9/2006 | Massengale et al. |
| 7,125,397 B2 | 10/2006 | Woehr et al. |
| 7,141,286 B1 | 11/2006 | Kessler et al. |
| 7,175,081 B2 | 2/2007 | Andreasson et al. |
| 7,182,256 B2 | 2/2007 | Andreasson et al. |
| 7,232,066 B2 | 6/2007 | Anderasson et al. |
| 7,240,926 B2 | 7/2007 | Dalle et al. |
| 7,299,981 B2 | 11/2007 | Hickle et al. |
| 7,374,555 B2 | 5/2008 | Heinz et al. |
| 7,404,500 B2 | 7/2008 | Marteau et al. |
| 7,410,803 B2 | 8/2008 | Nollert et al. |
| 7,425,208 B1 | 9/2008 | Vitello |
| 7,437,972 B2 | 10/2008 | Yeager |
| D581,046 S | 11/2008 | Sudo |
| D581,047 S | 11/2008 | Koshidaka |
| D581,049 S | 11/2008 | Sudo |
| 7,482,166 B2 | 1/2009 | Nollert et al. |
| D589,612 S | 3/2009 | Sudo |
| 7,497,330 B2 | 3/2009 | Anthony et al. |
| 7,503,453 B2 | 3/2009 | Cronin et al. |
| 7,588,563 B2 | 9/2009 | Guala |
| 7,594,681 B2 | 9/2009 | DeCarlo |
| 7,608,057 B2 | 10/2009 | Woehr et al. |
| 7,611,487 B2 | 11/2009 | Woehr et al. |
| 7,632,244 B2 | 12/2009 | Buehler et al. |
| D608,900 S | 1/2010 | Giraud et al. |
| 7,641,636 B2 | 1/2010 | Moesli et al. |
| D612,939 S | 3/2010 | Boone, III et al. |
| 7,681,606 B2 | 3/2010 | Khan et al. |
| 7,698,180 B2 | 4/2010 | Fago et al. |
| 7,735,664 B1 | 6/2010 | Peters et al. |
| 7,748,892 B2 | 7/2010 | McCoy |
| 7,762,988 B1 | 7/2010 | Vitello |
| 7,766,919 B2 | 8/2010 | Delmotte |
| 7,802,313 B2 | 9/2010 | Czajka |
| 7,886,908 B2 | 2/2011 | Farrar et al. |
| 7,918,830 B2 | 4/2011 | Langan et al. |
| 7,922,213 B2 | 4/2011 | Werth |
| 7,988,004 B1 | 8/2011 | Marret et al. |
| 8,034,041 B2 | 10/2011 | Domkowski et al. |
| 8,079,518 B2 | 12/2011 | Turner et al. |
| 8,091,727 B2 | 1/2012 | Domkowwski |
| 8,118,788 B2 | 2/2012 | Frezza |
| 8,137,324 B2 | 3/2012 | Bobst |
| 8,140,349 B2 | 3/2012 | Hanson et al. |
| 8,252,247 B2 | 8/2012 | Ferlic |
| 8,257,286 B2 | 9/2012 | Meyer et al. |
| 8,328,082 B1 | 12/2012 | Bochenko et al. |
| 8,348,895 B1 | 1/2013 | Vitello |
| 8,353,869 B2 | 1/2013 | Ranalletta et al. |
| 8,413,811 B1 | 4/2013 | Arendt |
| 8,443,999 B1 | 5/2013 | Reinders |
| D684,057 S | 6/2013 | Kwon |
| 8,512,277 B2 | 8/2013 | Del Vecchio |
| 8,528,757 B2 | 9/2013 | Bisio |
| 8,556,074 B2 | 10/2013 | Turner et al. |
| 8,579,116 B2 | 11/2013 | Pether et al. |
| 8,591,462 B1 | 11/2013 | Vitello |
| 8,597,255 B2 | 12/2013 | Emmott et al. |
| 8,597,271 B2 | 12/2013 | Langan et al. |
| 8,616,413 B2 | 12/2013 | Koyama |
| D701,304 S | 3/2014 | Lair et al. |
| 8,672,902 B2 | 3/2014 | Ruan et al. |
| 8,702,674 B2 | 4/2014 | Bochenko |
| 8,777,910 B2 | 7/2014 | Bauss et al. |
| 8,777,930 B2 | 7/2014 | Swisher et al. |
| 8,852,561 B2 | 10/2014 | Wagner et al. |
| 8,864,021 B1 | 10/2014 | Vitello |
| 8,864,707 B1 | 10/2014 | Vitello |
| 8,864,708 B1 | 10/2014 | Vitello |
| 8,911,424 B2 | 12/2014 | Weadock et al. |
| 8,945,082 B2 | 2/2015 | Geiger et al. |
| 9,016,473 B2 | 4/2015 | Tamarindo |
| 9,082,157 B2 | 7/2015 | Gibson |
| 9,101,534 B2 | 8/2015 | Bochenko |
| D738,495 S | 9/2015 | Strong et al. |
| 9,125,976 B2 | 9/2015 | Uber, III et al. |
| D743,019 S | 11/2015 | Schultz |
| 9,199,042 B2 | 12/2015 | Farrar et al. |
| 9,199,749 B1 | 12/2015 | Vitello et al. |
| 9,220,486 B2 | 12/2015 | Schweiss et al. |
| 9,220,577 B2 | 12/2015 | Jessop et al. |
| D750,228 S | 2/2016 | Strong et al. |
| 9,272,099 B2 | 3/2016 | Limaye et al. |
| 9,311,592 B1 | 4/2016 | Vitello et al. |
| D756,777 S | 5/2016 | Berge et al. |
| 9,336,669 B2 | 5/2016 | Bowden et al. |
| D759,486 S | 6/2016 | Ingram et al. |
| D760,384 S | 6/2016 | Niunoya et al. |
| D760,902 S | 7/2016 | Persson |
| 9,402,967 B1 | 8/2016 | Vitello |
| 9,427,715 B2 | 8/2016 | Palazzolo et al. |
| 9,433,768 B2 | 9/2016 | Tekeste et al. |
| 9,463,310 B1 | 10/2016 | Vitello |
| D773,043 S | 11/2016 | Ingram et al. |
| D777,903 S | 1/2017 | Schultz |
| 9,662,456 B2 | 5/2017 | Woehr |
| D789,529 S | 6/2017 | Davis et al. |
| 9,687,249 B2 | 6/2017 | Hanlon et al. |
| 9,744,304 B2 | 8/2017 | Swift et al. |
| D797,928 S | 9/2017 | Davis et al. |
| D797,929 S | 9/2017 | Davis et al. |
| 9,764,098 B2 | 9/2017 | Hund et al. |
| 9,821,152 B1 | 11/2017 | Vitello et al. |
| D806,241 S | 12/2017 | Swinney et al. |
| D807,503 S | 1/2018 | Davis et al. |
| 9,855,191 B1 | 1/2018 | Vitello et al. |
| D815,945 S | 4/2018 | Fischer |
| 9,987,438 B2 | 6/2018 | Stillson |
| D825,746 S | 8/2018 | Davis et al. |
| 10,039,913 B2 | 8/2018 | Yeh et al. |
| D831,201 S | 10/2018 | Holtz et al. |
| D834,187 S | 11/2018 | Ryan |
| 10,124,122 B2 | 11/2018 | Zenker |
| 10,166,343 B1 | 1/2019 | Hunt et al. |
| 10,166,347 B1 | 1/2019 | Vitello |
| 10,183,129 B1 | 1/2019 | Vitello |
| 10,207,099 B1 | 2/2019 | Vitello |
| D842,464 S | 3/2019 | Davis et al. |
| D847,373 S | 4/2019 | Hurwit et al. |
| 10,300,263 B1 | 5/2019 | Hunt |
| 10,307,548 B1 | 6/2019 | Hunt et al. |
| 10,315,024 B1 | 6/2019 | Vitello et al. |
| 10,315,808 B2 | 6/2019 | Taylor et al. |
| 10,376,655 B2 | 8/2019 | Pupke et al. |
| D859,125 S | 9/2019 | Weagle et al. |
| 10,478,262 B2 | 11/2019 | Niese et al. |
| 10,758,684 B1 | 9/2020 | Vitello et al. |
| 10,773,067 B2 | 9/2020 | Davis et al. |
| 10,888,672 B1 | 1/2021 | Vitello |
| 10,898,659 B1 | 1/2021 | Vitello et al. |
| 10,912,898 B1 | 2/2021 | Vitello et al. |
| 10,933,202 B1 | 3/2021 | Banik |

(56) References Cited

U.S. PATENT DOCUMENTS

| | | |
|---|---|---|
| 10,953,162 B1 | 3/2021 | Hunt et al. |
| 11,040,149 B1 | 6/2021 | Banik |
| 11,040,154 B1 | 6/2021 | Vitello et al. |
| 11,097,071 B1 | 8/2021 | Hunt et al. |
| 11,278,681 B1 | 3/2022 | Banik et al. |
| D948,713 S | 4/2022 | Banik |
| 11,357,588 B1 | 6/2022 | Vitello et al. |
| 11,413,406 B1 | 8/2022 | Vitello et al. |
| 11,426,328 B1 | 8/2022 | Ollmann et al. |
| 11,471,610 B1 | 10/2022 | Banik et al. |
| 11,523,970 B1 | 12/2022 | Vitello et al. |
| 11,541,180 B1 | 1/2023 | Vitello et al. |
| 11,690,994 B1 | 7/2023 | Banik et al. |
| 11,697,527 B1 | 7/2023 | Hendren et al. |
| 11,779,520 B1 | 10/2023 | Vitello |
| 11,793,987 B1 | 10/2023 | Vitello et al. |
| 11,857,751 B1 | 1/2024 | Vitello |
| 11,872,187 B1 | 1/2024 | Vitello et al. |
| 11,904,149 B1 | 2/2024 | Vitello et al. |
| 11,911,339 B1 | 2/2024 | Lehel et al. |
| 2001/0056258 A1 | 12/2001 | Evans |
| 2002/0023409 A1 | 2/2002 | Py |
| 2002/0046962 A1 | 4/2002 | Vallans et al. |
| 2002/0079281 A1 | 6/2002 | Hierzer et al. |
| 2002/0097396 A1 | 7/2002 | Schafer |
| 2002/0099334 A1 | 7/2002 | Hanson et al. |
| 2002/0101656 A1 | 8/2002 | Blumenthal et al. |
| 2002/0104770 A1 | 8/2002 | Shapeton et al. |
| 2002/0133119 A1 | 9/2002 | Eakins et al. |
| 2003/0055685 A1 | 3/2003 | Cobb et al. |
| 2003/0146617 A1 | 8/2003 | Franko, Sr. |
| 2003/0183547 A1 | 10/2003 | Heyman |
| 2003/0187403 A1 | 10/2003 | Balestracci |
| 2004/0008123 A1 | 1/2004 | Carrender et al. |
| 2004/0064095 A1 | 4/2004 | Vitello |
| 2004/0116858 A1 | 6/2004 | Heinz et al. |
| 2004/0173563 A1 | 9/2004 | Kim et al. |
| 2004/0186437 A1 | 9/2004 | Frenette et al. |
| 2004/0225258 A1 | 11/2004 | Balestracci |
| 2005/0146081 A1 | 7/2005 | MacLean et al. |
| 2005/0148941 A1 | 7/2005 | Farrar et al. |
| 2005/0209555 A1 | 9/2005 | Middleton et al. |
| 2006/0084925 A1 | 4/2006 | Ramsahoye |
| 2006/0089601 A1 | 4/2006 | Dionigi |
| 2006/0169611 A1 | 8/2006 | Prindle |
| 2006/0173415 A1 | 8/2006 | Cummins |
| 2006/0189933 A1 | 8/2006 | Alheidt et al. |
| 2007/0060898 A1 | 3/2007 | Shaughnessy et al. |
| 2007/0106234 A1 | 5/2007 | Klein |
| 2007/0142786 A1 | 6/2007 | Lampropoulos et al. |
| 2007/0191690 A1 | 8/2007 | Hasse et al. |
| 2007/0219503 A1 | 9/2007 | Loop et al. |
| 2007/0257111 A1 | 11/2007 | Ortenzi |
| 2008/0068178 A1 | 3/2008 | Meyer |
| 2008/0097310 A1 | 4/2008 | Buehler et al. |
| 2008/0106388 A1 | 5/2008 | Knight |
| 2008/0140020 A1 | 6/2008 | Shirley |
| 2008/0243088 A1 | 10/2008 | Evans |
| 2008/0303267 A1 | 12/2008 | Schnell et al. |
| 2008/0306443 A1 | 12/2008 | Neer |
| 2009/0084804 A1 | 4/2009 | Caspary et al. |
| 2009/0099552 A1 | 4/2009 | Levy et al. |
| 2009/0149815 A1 | 6/2009 | Kiel et al. |
| 2009/0166311 A1 | 7/2009 | Claessens |
| 2009/0326481 A1 | 12/2009 | Swisher et al. |
| 2010/0050351 A1 | 3/2010 | Colantonio et al. |
| 2010/0051491 A1 | 3/2010 | Lampropoulos et al. |
| 2010/0084403 A1 | 4/2010 | Popish et al. |
| 2010/0126894 A1 | 5/2010 | Koukol et al. |
| 2010/0179822 A1 | 7/2010 | Reppas |
| 2010/0211016 A1* | 8/2010 | Palmer-Felgate ... A61M 5/3202 141/2 |
| 2010/0228226 A1 | 9/2010 | Nielsen |
| 2010/0252564 A1 | 10/2010 | Martinez et al. |
| 2010/0283238 A1 | 11/2010 | Deighan et al. |
| 2011/0044850 A1 | 2/2011 | Solomon et al. |
| 2011/0046550 A1 | 2/2011 | Schiller et al. |
| 2011/0046603 A1 | 2/2011 | Felsovalyi et al. |
| 2012/0064515 A2 | 3/2012 | Knapp et al. |
| 2012/0096957 A1 | 4/2012 | Ochman |
| 2012/0110950 A1 | 5/2012 | Schraudolph |
| 2013/0018356 A1 | 1/2013 | Prince et al. |
| 2013/0056130 A1 | 3/2013 | Alpert et al. |
| 2013/0088354 A1 | 4/2013 | Thomas |
| 2013/0237949 A1 | 9/2013 | Miller |
| 2013/0269592 A1 | 10/2013 | Heacock et al. |
| 2014/0000781 A1 | 1/2014 | Franko, Jr. |
| 2014/0034536 A1 | 2/2014 | Reinhardt et al. |
| 2014/0069202 A1 | 3/2014 | Fisk |
| 2014/0069829 A1 | 3/2014 | Evans |
| 2014/0076840 A1 | 3/2014 | Graux et al. |
| 2014/0135738 A1 | 5/2014 | Panian |
| 2014/0155868 A1 | 6/2014 | Nelson et al. |
| 2014/0163465 A1 | 6/2014 | Bartlett, II et al. |
| 2014/0257843 A1 | 9/2014 | Adler et al. |
| 2014/0326727 A1 | 11/2014 | Jouin et al. |
| 2014/0353196 A1 | 12/2014 | Key |
| 2015/0013811 A1 | 1/2015 | Carrel et al. |
| 2015/0048045 A1 | 2/2015 | Miceli et al. |
| 2015/0112296 A1 | 4/2015 | Ishiwata et al. |
| 2015/0136632 A1 | 5/2015 | Moir et al. |
| 2015/0182686 A1 | 7/2015 | Okihara |
| 2015/0191633 A1 | 7/2015 | De Boer et al. |
| 2015/0246185 A1 | 9/2015 | Heinz |
| 2015/0302232 A1 | 10/2015 | Strassburger et al. |
| 2015/0305982 A1 | 10/2015 | Bochenko |
| 2015/0310771 A1 | 10/2015 | Atkinson et al. |
| 2016/0067144 A1 | 3/2016 | Chang |
| 2016/0067422 A1 | 3/2016 | Davis et al. |
| 2016/0090456 A1 | 3/2016 | Ishimaru et al. |
| 2016/0136352 A1 | 5/2016 | Smith et al. |
| 2016/0144119 A1 | 5/2016 | Limaye et al. |
| 2016/0158110 A1 | 6/2016 | Swisher et al. |
| 2016/0158449 A1 | 6/2016 | Limaye et al. |
| 2016/0176550 A1 | 6/2016 | Viitello et al. |
| 2016/0194121 A1 | 7/2016 | Ogawa et al. |
| 2016/0250420 A1 | 9/2016 | Maritan et al. |
| 2016/0279032 A1 | 9/2016 | Davis |
| 2016/0328586 A1 | 11/2016 | Bowden et al. |
| 2016/0361235 A1 | 12/2016 | Swisher |
| 2016/0367439 A1 | 12/2016 | Davis et al. |
| 2017/0007771 A1 | 1/2017 | Duinat et al. |
| 2017/0014310 A1 | 1/2017 | Hyun et al. |
| 2017/0124289 A1 | 5/2017 | Hasan et al. |
| 2017/0173321 A1 | 6/2017 | Davis et al. |
| 2017/0203086 A1 | 7/2017 | Davis |
| 2017/0225843 A1 | 8/2017 | Glaser et al. |
| 2017/0239141 A1 | 8/2017 | Davis et al. |
| 2017/0297781 A1 | 10/2017 | Kawamura |
| 2017/0319438 A1 | 11/2017 | Davis et al. |
| 2017/0354792 A1 | 12/2017 | Ward |
| 2018/0001540 A1 | 1/2018 | Byun |
| 2018/0014998 A1 | 1/2018 | Yuki et al. |
| 2018/0064604 A1 | 3/2018 | Drmanovic |
| 2018/0078684 A1 | 3/2018 | Peng et al. |
| 2018/0089593 A1 | 3/2018 | Patel et al. |
| 2018/0098915 A1 | 4/2018 | Rajagopal et al. |
| 2018/0147115 A1 | 5/2018 | Nishioka et al. |
| 2018/0312305 A1* | 11/2018 | Rognard ............ B65D 47/0852 |
| 2019/0308006 A1 | 10/2019 | Erekovcanski et al. |
| 2019/0388626 A1 | 12/2019 | Okihara |
| 2022/0008645 A1 | 1/2022 | Ukai et al. |

FOREIGN PATENT DOCUMENTS

| | | |
|---|---|---|
| EP | 269920 | 6/1988 |
| GB | 486367 | 6/1938 |
| JP | 08002544 | 1/1996 |
| KR | 101159987 | 6/2012 |
| WO | WO2008000279 | 1/2008 |
| WO | WO2017086607 | 5/2015 |

* cited by examiner

SNAP ACTION TAMPER EVIDENT CLOSURE ASSEMBLY

BACKGROUND OF THE INVENTION

The present application is based on and a claim of priority is made under 35 U.S.C. Section 119(e) to a provisional patent application that is currently pending in the U.S. Patent and Trademark Office, namely, that having Ser. No. 63/125,156 and a filing date of Dec. 14, 2020, and which is incorporated herein by reference.

FIELD OF THE INVENTION

This invention relates to a closure for a syringe or other medical container having tamper evident capabilities and including a tip cap removably retained within the interior of an outer cover without the use of frangible structure interconnecting components of the closure. An outward flexure of a portion of the closure at least partially defines a snap-action disconnection of said tip cap from within an interior of the cover.

DESCRIPTION OF THE RELATED ART

In numerous medical care facilities, it is common practice to administer various medications to a patient either orally or by injection. As a result, a number of syringes, IV bags, medication carrying containers, etc. may be pre-loaded within or supplied to the medical care facility and subsequently stored at different locations stations throughout the facility. At large medical facilities, preloaded syringes or other administering containers may be delivered to multiple nurses' stations. Because of the remote location of many nurse's stations, a pre-loaded syringe is very often given to other personnel for delivery or subsequent dosing of the patient by a duly qualified nurse or other medically trained person.

Also, in the case of a very expensive drug or an addictive type drug such as, but not limited to, morphine, there is a danger that the pre-loaded container will be tampered with at some point, by a person seeking to improperly gain unauthorized access to the drug. This possibility can present real danger when unauthorized access to the contents of the preloaded syringe, IV bag or other container is accomplished. One possible outcome of such a situation includes the inappropriate substitution of some other, unauthorized material in the syringe, IV container, etc. By way of example only, if saline solution were substituted for a dose of morphine, this could have extremely serious consequences. Thus, there is a problem of determining if a sealed, preloaded medication container has, or has not, been exposed to contamination or might otherwise have been compromised by it being tampered with. This and related types of problems have been described in U.S. Pat. No. 4,667,837 and in other patents, such as U.S. Pat. No. 5,328,474 granted previously to one or more of the named inventors herein and/or owned by their Assignee.

However, certain problems remain in the relevant field of art, despite the introduction of products represented in the above noted patents. Such problems are related to the manufacturing thereof in a manner which is relatively easy and inexpensive, as well as some problems involved with the assembly and placement of a protective, tamper evident structure onto a drug loaded container. Also, additional problems relate to the maintenance of sterility during storage at the manufacturing facility and during transport to and throughout the various medical facilities where they are used.

Further, known or conventional tamper evident tops typically rely on frangible and/or breakaway features. However, such frangible structures can be prone to breaking prematurely, even under normal shipping and handling conditions. If the closure breaks "accidentally" during manufacturing, transit or handling, the cost is relatively low in that it is limited to the disposal of the closure itself. However, if the closure breaks after being installed on a pre-filled syringe or other medical container, the cost may be considerably higher considering that the pre-filled syringe, etc. must also be disposed of.

In addition, use of medical closures incorporating breakaway components can result in the loose pieces being inadvertently discarded from the closure. This is particularly important in certain medical procedures, including surgery, especially if any such loose pieces were to enter the body of a patient, which could possibly result in serious damage to the patient. Moreover, structures of medical closures that rely on frangible features which may separate or "break" into a plurality of pieces during use have sometimes addressed the resulting problem by attempts to capture the broken/loose pieces in some manner.

Therefore, there is a need in the medical field and related areas of commerce for a medical closure, which may have tamper evident capabilities and which eliminates the use of frangible components or features substantially, if not completely. Moreover, if any such improved medical closure assembly were developed, it would preferably also offer a cost-effective solution for a Tamper Evident Closure or Cap (TEC) that meets all of the common/standard user needs including, but not necessarily limited to, reliability, simplicity of use, minimization or elimination of loose parts, and biocompatibility. Further, if any such improved medical closure were developed it would ideally also be structured to include or offer a snap fit type of construction.

SUMMARY OF THE INVENTION

Accordingly, the present invention seeks to address such problems and others associated with the handling of medical tamper evident closures structured for use with medication administering or storage containers during their manufacture, assembly, and administration.

As such and as illustrated in the drawings, the present invention is directed to a closure for a medical container having tamper evident capabilities which provide a clear indication that access to a syringe or other medical container, to which the closure is attached, has been attempted or accomplished. Moreover, at least some of the disadvantages and problems of the type set forth above and otherwise commonly associated with known or conventional tamper evident caps (TEC) has been overcome through the elimination of frangible or breakaway connections, components, etc.

Accordingly, the one or more preferred embodiments of the present invention include a tamper evident closure including an exterior cover which may be in the form of a sleeve-like structure having an at least partially hollow interior. In addition, the cover includes an access opening formed at one end thereof and an oppositely disposed closed-end. Further, the at least partially hollow interior of the cover is sufficiently dimensioned and configured to at least partially enclose a tip cap. The tip cap is removably retained within the interior of the cover and may be any one of a different category of structures, such as those commonly referred to in the medical industry as Lure, enteral, oral, neuraxial, etc.

As indicated herein, the various embodiments of the closure assembly of the present invention are structured to eliminate the utilization of frangible and/or breakaway type of components. Therefore, each of the one or more embodiments of the closure includes a first snap structure disposed within the cover and a second snap structure disposed on and movable with the removably retained tip cap. As such, the first and second snap structures are cooperatively disposed and configured to removably restrict exiting or removal of the tip cap from within the cover, such as through the access opening. However, as will be apparent securement of the tip cap to an appropriately structured or configured medical container, such as a syringe, will facilitate easy and effective removal of the tip cap from the cover, as intended. The first and second snap structures are disposed in movable engagement with one another, concurrent to the exiting or removal of the tip cap through the access opening.

Accordingly, at least one preferred embodiment of the tamper evident closure (TEC) of the present invention includes each of the first and second snap structures having an angled segment disposed thereon. The angled segments of each of the first and second snap structures are disposed in sliding engagement with one another, concurrent to the exiting or removal of the tip cap, through the access opening, as set forth above. In addition, removal of the tip cap from the cover is further facilitated by the cover being dimensioned and configured to define an "outward flexure" thereof concurrent to the first and second snap structures and more specifically the respective angled segments, being disposed in movable, sliding engagement with one another. In addition, the outward flexure of the cover occurring concurrent to the sliding engagement of the angled segments defines a "snap-action" disconnection of the tip cap from the cover as the first and second snap structures disengage from one another and further as the tip cap passes outwardly from the interior of the cover through the aforementioned access opening.

As indicated, the one or more embodiments of the closure of the present invention include tamper evident capabilities. Therefore, in at least one embodiment each of the first and second snap structures, in addition to the aforementioned angled segments, also include a stop segment. Each stop segment is formed on or connected to and movable with corresponding ones of the first and second snap structures and are disposable in abutting relation to one another upon an attempted reinsertion of the tip cap back into the interior of the cover. Such abutting engagement between the stop segments of the first and second snap structure prevent a complete reinsertion of the tip cap into the interior of the cover, thereby preventing disposition of the tip cap back into its original, operative, removably retained position. As a result, failure to reinsert the tip cap into the interior of the cover in its original, operative position will provide a clear indication that the tip cap and cover have been previously separated in an authorized or unauthorized (tampering) use of the closure.

As will be explained in greater detail hereinafter, the angled segments of the first and second snap structures may preferably be disposed at a substantially 120° angle relative respectively to the inner surface of the cover and the outer surface of the tip cap. Also, the stop segments of each of the first and second snap structures are respectfully disposed in substantially perpendicular relation respectively relative to the inner surface of the cover and the outer surface of the tip cap.

Yet additional structural and operative features of at least one embodiment of the TEC of the present invention include the first snap structure integrally formed or fixedly connected to an inner surface of the cover. In cooperation therewith, the second snap structure is integrally formed on and/or fixedly connected to the outer surface of the tip cap. Further, the disposition of the first and second snap structures, respectively on the inner surface of the cover and the outer surface of the tip cap is such as to facilitate their engagement, via the aforementioned angled segments, in a manner which will removably restrict exiting of the tip cap from the interior of the cover through the access opening. Similarly, the disposition and structuring of the first and second snap segments will prevent complete or total reinsertion of the tip cap into the interior of the cover, via the aforementioned stop segments, into the original, operative position of the tip cap, prior to its removal when connected to an appropriately configured syringe or other medical container/device. In order to assure intended engagement between the angled segments as well as the stop segments on the first and second snap connectors, at least one but preferably both of the first and second snap connectors have a continuous and/or annular configuration, as well as the angled segments and stop segments respectively formed thereon.

In at least one additional preferred embodiment, the TEC includes the first snap connector disposed within the interior of the cover concurrent to the second snap connector disposed on an exterior surface of the tip cap. However, this at least one additional embodiment comprises the inclusion of an indicator member having an annular or ring-like configuration. Further, the first snap structure is formed on an interior surface of the indicator member or indicator ring rather than on the interior surface of the cover. Therefore, the removable retention and/or exit restricting, retaining relation of the tip cap within the interior of the cover is accomplished by virtue of engagement of the first and second snap structures.

Additional structural and operative features of this additional preferred embodiment of the TEC includes the aforementioned exit retaining relation of the tip cap occurring concurrently to the indicator member or ring being initially maintained in a "trapped" orientation between the tip cap and an interior surface of the cover. Further, the indicator ring is disposed and dimension to be disposed in surrounding relation to the tip cap in order to facilitate initial engagement of the first and second snap connectors with one another, prior to the removal of the tip cap from the interior of the cover. As such, the outer diameter of the indicator ring is greater than the inner diameter of the access opening and/or a corresponding diametrical dimension of an interior surface portion or "shelf" of the cover. As a result, upon detachment of the tip cap from the indicator ring, concurrent to its removal through the access opening, the indicator ring will be prevented from moving with the tip cap from within the interior of the cover.

Therefore, due to the interaction of the first and second snap structures on the indicator ring and the tip cap respectively, as well as the larger diametrical dimension of the indicator ring, the indicator ring will be "captured" within a remainder or chamber portion of the interior of the cover. In more specific terms, the indicator ring will move or be forced, at least partially due to the influence of gravity thereon, from the "trapped" orientation into the "captured"

orientation, concurrent and/or subsequent to a snap-action detachment of the tip cap from the indicator ring.

Yet additional features of this additional one or more preferred embodiments of the TEC of the present invention include each of the first and second snap structures having an angled segment integrally or fixedly formed thereon, so as to move therewith. The angled segments of the first and second snap structures of this additional embodiment can be structurally and/or operationally equivalent or at least similar to those described with the above-noted other embodiment of the TEC. Therefore, the angled segments of the first and second snap structures respectively associated with the indicator ring and the tip cap are disposed in movable, sliding engagement with one another, concurrent to the exiting or removal of the tip cap through the access opening, such as when the tip cap is connected to a syringe or other appropriately configured medical container or device. Further, the indicator member is dimensioned and structured to define an outward flexure thereof, concurrent to the sliding engagement of said angled segments. This at least minimal outward flexure will facilitate the aforementioned movable sliding engagement and disconnection of the angled segments of the first and second snap structures. In turn, at least a minimal outward flexure of the indicator ring will at least partially define a snap-action disconnection of said first and second snap structures as well as a snap-action disconnection of the tip cap from said indicator member, when the indicator member is in the aforementioned trapped orientation.

However, one distinguishing structural feature in the one or more additional embodiments of the TEC of the present invention comprises an absence of the aforementioned stop segments on the first and second snap structures. As a result, the tip cap may be capable of being reinserted into the interior of the cover. However, when the indicator ring is disposed in the aforementioned "captured" orientation it will generally be disposed in supported relation on the interior surface of the bottom or closed-end of the cover. In turn, the second snap structure disposed on the exterior surface of the tip cap will be sufficiently spaced from the indicator ring, even when the tip cap is fully re-inserted on the interior of the cover to prevent reattachment or engagement of the first and second snap structures. Therefore, the aforementioned tamper evident capabilities of this additional one or more embodiments of the TEC of the present invention will be at least partially defined by a failure to retain the tip cap within the cover and/or establish a reconnection or attachment between the first and second snap structures of the indicator ring and the tip cap.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

The invention will now be described more fully hereinafter with reference to the accompanying drawings in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

With initial reference to FIGS. 1-3A, the present invention is directed to a tamper evident closure generally indicated as 10 including an exterior cover 12 which may be in the form of a sleeve-like configuration. In addition, the cover 12 has an at least partially hollow interior 14 disposed in direct communication with an access opening 16 disposed at one end thereof. A closed-end 18 covers the opposite end of the cover 12 relative to the access opening 16. Further, the at least partially hollow interior 14 of the cover 12 is sufficiently dimensioned and configured to at least partially enclose a tip cap 20. The tip cap 20 is removably retained within the interior 14 of the cover 12 and may be any one of a plurality of different categories of tip cap structures, such as those commonly referred to in the medical industry as Lure, enteral, oral, neuraxial, etc.

For reasons which will be more evident based on the included description of the one or more embodiments of the closure 10 of the present invention, insertion of the tip cap 20 into the interior 14 of the cover 12 may be more efficiently accomplished by inserting it through one end of the cover, oppositely disposed to the access opening 16 and thereafter securing the closed end to the one end, such as by sonic welding or the like.

Figure 1:
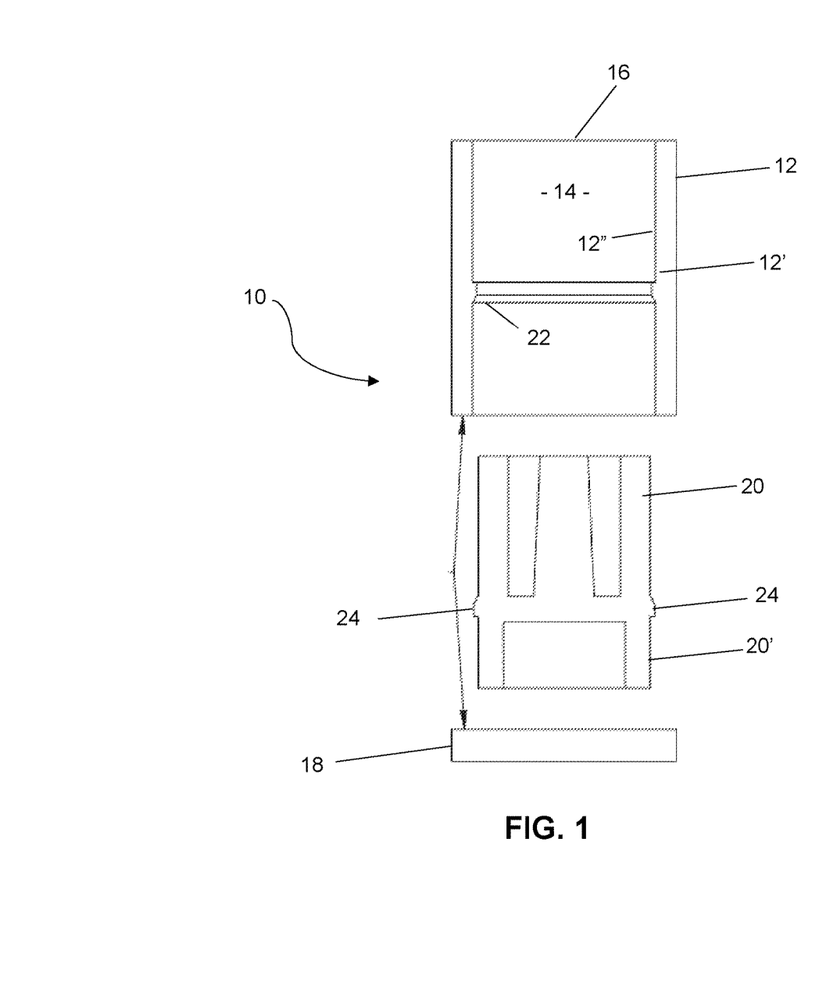
FIG. 1 is an exploded view of one embodiment of the closure assembly of the present invention.
Figure 2:
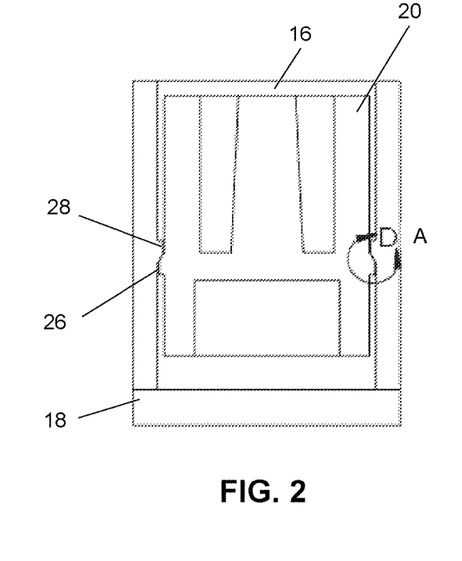
FIG. 2 is an interior view of the closure assembly of the embodiment of FIG. 1 in assembled form.
Figure 2A:
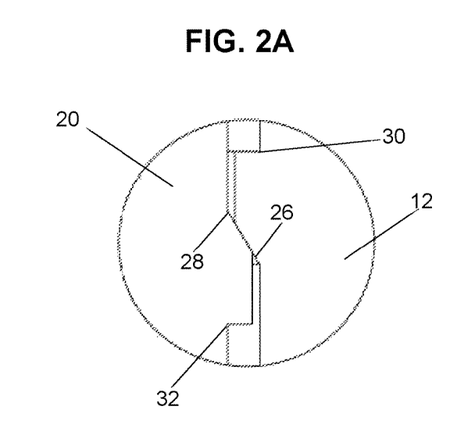
FIG. 2A is a detailed view of the indicated structure "A" of the embodiment of FIG. 2.
Figure 3:
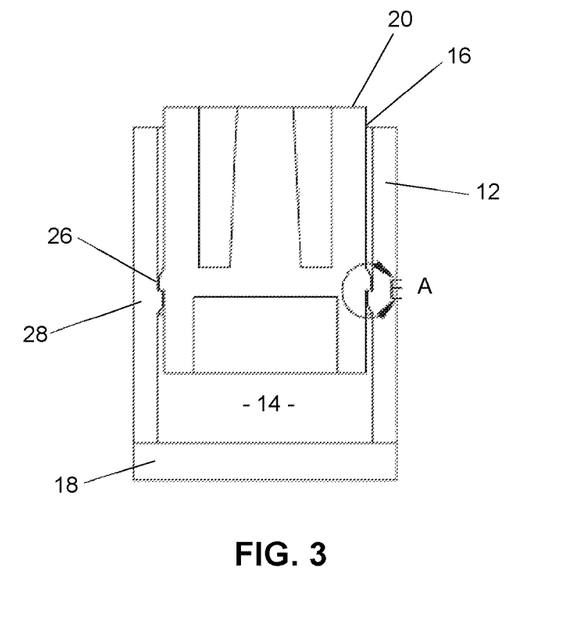
FIG. 3 is an interior view of the embodiment represented in FIG. 1-2A representing an attempted re-insertion of a tip cap into the interior of a surrounding cover, subsequent to its removal therefrom.
Figure 3A:
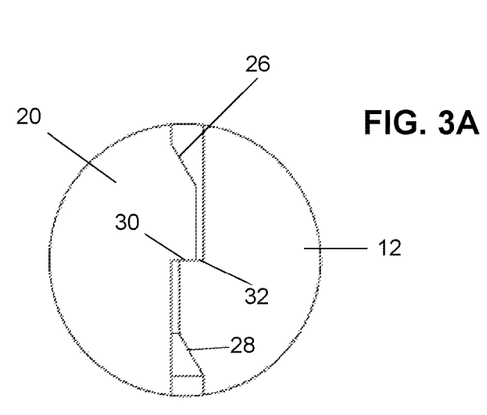
FIG. 3A is a detailed view of the indicated structure "A" of the embodiment of FIG. 3.

As emphasized, the one or more preferred embodiments of the closure 10 of the present invention are structured to eliminate the utilization of frangible and/or breakaway type of components or connections. Therefore, each of the one or more embodiments of the closure 10, 10' (see FIGS. 4-6) includes a first snap structure 22 disposed within the interior 14 cover 12 and a second snap structure 24 disposed on and movable with the removably retained tip cap 20. As such, the first and second snap structures 22 and 24 are cooperatively disposed and configured to removably restrict exiting or removal of the tip cap 20 from within the interior 14 of the cover 12, through the access opening 16. However as will be apparent, securement of the tip cap 20 to an appropriately structured or configured medical container (not shown for purposes of clarity), such as a syringe, will facilitate easy and effective removal of the tip cap 20 from the cover 12, through the exertion of an outward, axial or other appropriately directed separating force applied to the syringe, when attached to the tip cap 20 and or to both the syringe and the cover 12. As represented in FIGS. 2, the first and second snap structures 22 and 24 are initially disposed in engagement with one another, and are slidingly movable relative to one another concurrent to the exiting or removal of the tip cap 20 through the access opening 16. However, prior to removal of the tip 20 from the interior 14 of the cover 12, the engagement between the first and second snap structures 22 and 24, as represented in FIG. 2 will serve to retain the tip cap 20 within the interior 14 of the cover 12.

In more specific terms, at least one preferred embodiment of the tamper evident closure (TEC), as represented in FIGS. 1-3A, includes each of the first and second snap structures 22 and having an angled segment 26 and 28 disposed thereon. The angled segments 26 and 28 of each of the first and second snap structures 22 and 24 are disposed in sliding engagement with one another, concurrent to the exiting or removal of the tip cap 20, through the access opening 16, as set forth above. In addition, removal of the tip cap 20 from the cover 12 is further facilitated by the cover 12 incorporating a "flexible construction". By way of nonlimiting example, the flexible construction of the cover 12 may be defined by its formation from an at least minimally flexible material and/or the dimensioning of at least a portion of the sidewall 12' being sufficiently thin to allow a flexing thereof, such as when a flexing force is exerted thereon.

Therefore, the cover 12 and/or at least a portion thereof is dimensioned and/or structured to define an "outward flexure" thereof concurrent to the first and second snap structures 22 and 24 and more specifically the respective angled segments 26 and 28, movably and slidingly engaging with one another. As indicated, such movable, sliding engagement between the confronting surfaces of the respective angled segments 26 and 28 occurs concurrent to the tip cap 20, once attached to a syringe, being forced outwardly from the interior 14 of the cover 12, through the access opening 16. In addition, the outward flexure of the cover 12 occurring concurrent to the sliding engagement of the angled segments defines a "snap-action" disconnection of the tip cap 20 from the cover 12 as the first and second snap structures 22 and 24 disengage from one another and further as the tip cap 20 passes outwardly from the interior 14 of the cover through the aforementioned access opening 16.

As indicated, the one or more embodiments of the closure 10, 10' of the present invention include tamper evident capabilities. Therefore, in at least one embodiment as represented in FIGS. 1-3A, each of the first and second snap structures 22 and 24, in addition to the aforementioned angled segments 26 and 28, also include a stop segment 30 and 32. Each stop segment 30 and 32 is formed on or connected to and movable with corresponding ones of the first and second snap structures 22 and 24 and are disposable in abutting relation to one another, as represented in FIGS. and 3A, upon an attempted reinsertion of the tip cap 20 back into the interior 14 of the cover. Such abutting engagement between the stop segments 30 and 32 of the first and second snap structure 22 and 24 prevent a complete reinsertion of the tip cap 20 into the interior 14 of the cover 12, thereby preventing disposition and retention of the tip cap 20 back into its original, operative, removably retained position, such as represented in FIG. 2. As a result, failure to reinsert and retain the tip cap into the interior 14 of the cover 12 in its original, operative position will provide a clear indication that the tip cap 20 and cover 12 have been previously separated in an authorized or unauthorized (tampering) use of the closure 10.

As will be explained in greater detail hereinafter, the angled segments 26 and 28 of the first and second snap structures 22 and 24 may preferably be disposed at, but not limited to, a substantially 120° angle relative respectively to the inner surface of the cover 12 and the outer surface of the tip cap 20. Also, the stop segments 30 and 32 of each of the first and second snap structures 22 and 24 are respectfully disposed in substantially perpendicular relation to the inner surface of the cover 12 and the outer surface of the tip cap 20, respectively. However, it is emphasized that the stop segments 30 and 32 may be located at angular orientations other than perpendicular, where in such other angular orientations would be sufficient to prevent passage and retention of the tip cap 20 back into the interior 14 of the cover 12.

Yet additional structural and operative features of one or more embodiments of the TEC of the present invention, as represented in FIGS. 1-3A, include the first snap structure 22 integrally formed on or fixedly connected to an inner surface 12" of the cover 12. In cooperation therewith, the second snap structure 24 is integrally formed on and/or fixedly connected to the outer surface 20' of the tip cap 20. Further, the disposition of the first and second snap structures 22 and 24, respectively on the inner surface 12" of the cover 12 and the outer surface 20' of the tip cap 20 is such as to facilitate their engagement, via the aforementioned angled segments 26 and 28, in a manner which will removably restrict exiting of the tip cap 20 from the interior 14 of the cover 12 through the access opening 16. Similarly, the disposition and structuring of the first and second snap segments 22 and 24 will prevent complete or total reinsertion and retention of the tip cap 20 into the interior 14 of the cover 12, via the aforementioned stop segments 30 and 32, into the original, operative position of the tip cap 20, subsequent to its removal when connected to an appropriately configured syringe or other medical container/device. In order to assure intended engagement between the angled segments 26 and 28 as well as the stop segments 30 and 32 on the first and second snap connectors 22 and 24, at least one but preferably both of the first and second snap connectors 22 and 24 have a continuous and/or annular configuration, extending continuously around the inner surface 12" and the outer surface 20' respectively, as well as the angled segments 22, 24 and stop segments 30, 32 respectively formed thereon.

Figure 4:
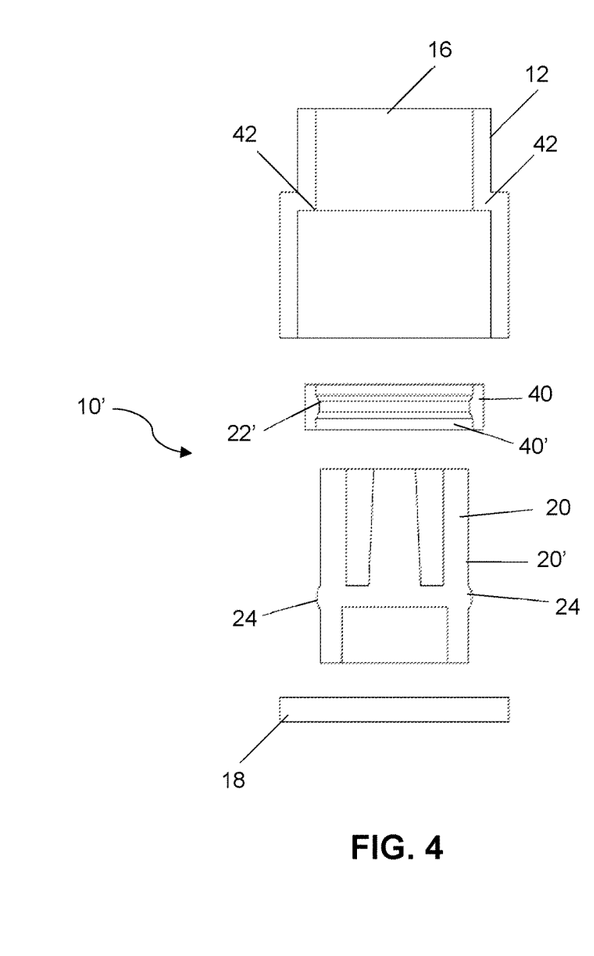
FIG. 4 is an exploded view of another embodiment of the closure assembly of the present invention operatively similar to the embodiments of the closure assembly as represented in FIGS. 1-3A.
Figure 5:
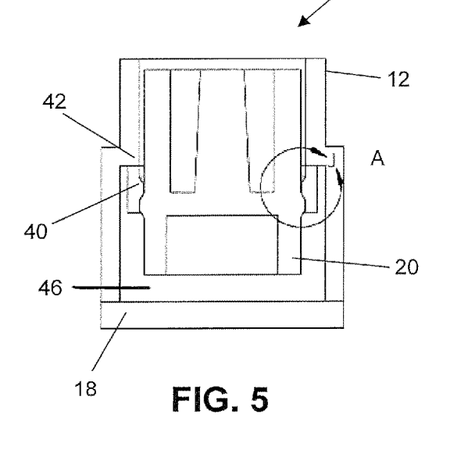
FIG. 5 is an interior view of the closure assembly of the embodiment of FIG. 4 in assembled form.
Figure 5A:
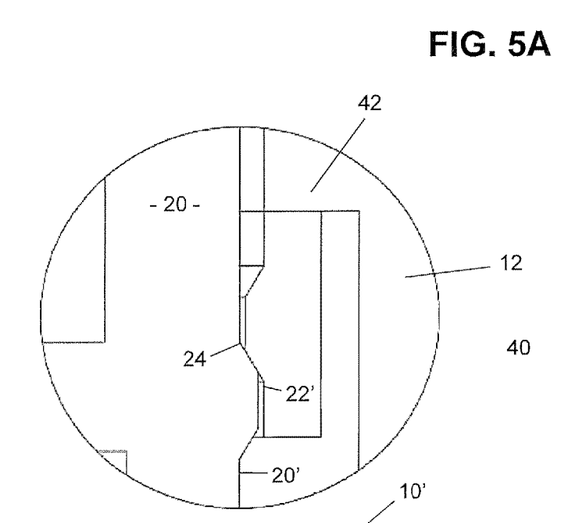
FIG. 5A is a detail view of the indicated structure "A" of the embodiment of FIG. 5.
Figure 6:
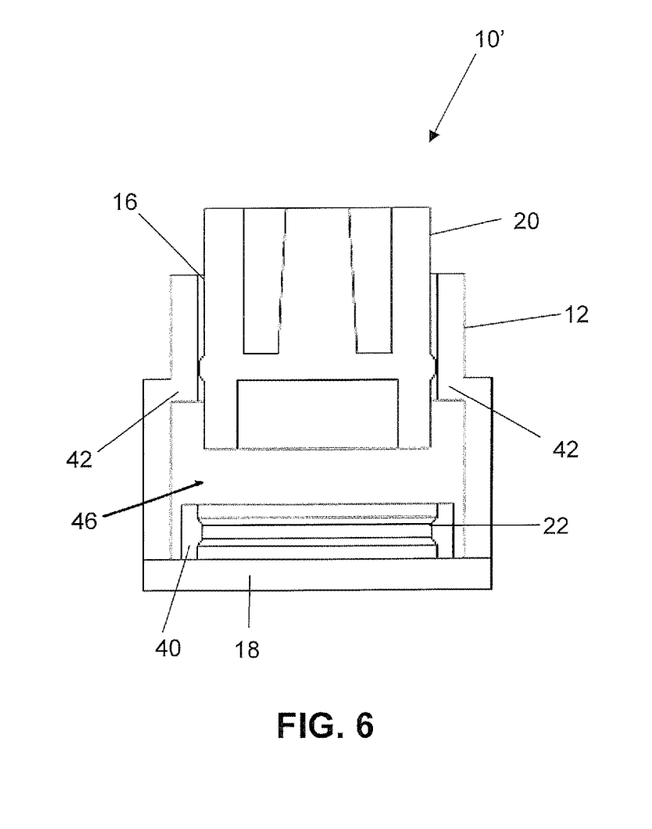
FIG. 6 is an interior view of the embodiment of FIGS. 4-5A representing an attempted re-insertion of a tip cap into the interior of a surrounding cover, subsequent to its removal therefrom.

In at least one additional embodiment as represented in FIGS. 4-6, the closure 10' includes the first snap connector 22' disposed within the interior 14 of the cover 12 concurrent to the second snap connector 24 disposed on an exterior surface 20' of the tip cap 20. However, this at least one additional embodiment comprises the inclusion of an indicator member 40 having an annular or ring-like configuration, as represented. Further, the first snap structure 22' is formed on an interior surface 40' of the indicator member or indicator ring 40 rather than on the interior surface 12" of the cover 12, as represented in FIGS. 1-3A. Therefore, the removable retention and/or exit restricting, retaining relation of the tip cap 20 within the interior 14 of the cover 12 is accomplished by virtue of engagement of the first and second snap structures 22' and 24.

Additional structural and operative features of this additional embodiment of the closure 10' includes the aforementioned exit retaining relation of the tip cap 20 occurring concurrently to the indicator member or ring 40 being initially maintained in a "trapped" orientation between the tip cap 20 and an interior surface of the cover 12", as represented in FIGS. 5 and 5A. Further, the indicator ring 40 is disposed and dimension to be disposed in surrounding relation to the tip cap in order to facilitate initial engagement of the first and second snap connectors 22' and with one another, prior to the removal of the tip cap 20 from the interior 14 of the cover 12, through the access opening 16. As such, the outer diameter of the indicator ring 40 is greater than the inner diameter of the access opening 16 and/or a corresponding diametrical dimension of an interior surface portion or "shelf" 42 of the cover 12.

More specifically, the interior 14 of the cover 12, as represented in FIGS. 4-6 includes an interior chamber 46 extending between inner surface of the cover which at least partially defines the shelf 42 and the interior surface of the closed-end 18. Moreover, an opening 48 into the interior of the chamber 46 is represented herein as defining the inner diameter of the shelf 42 and as such has a lesser diameter than that of the indicator ring 40. As a result, removal of the tip cap 20, such as one attached to a syringe, from the interior 14 of the cover 12 will result in the indicator ring 40 being forced out of its trapped orientation of FIG. 5 into a "captured" orientation as represented in FIG. 6. Such movement or positioning of the indicator ring 40 into the captured orientation will be due, at least in part, to the influence of gravity, in that the indicator ring 40 is movable within the interior 14 and chamber 46 of the cover 12, once it has been released from the trapped orientation and its engagement with the tip cap 20 as represented in FIGS. 5 and 5A. As a result, upon detachment of the tip cap 20 from the indicator ring 40, concurrent to its removal through the access opening 16, the indicator ring 40, due to its diameter being larger than that of the inner diameter 48 of the shelf 42, will be prevented from moving with the tip cap 20 from within the interior of the cover 12 through the access opening 16.

Therefore, due to the interaction of the first and second snap structures 22' in 24 on the indicator ring 40 and the tip cap 20 respectively, as well as the larger diametrical dimension of the indicator ring 40, the indicator ring 40 will be "captured" within chamber 46 of the interior of the cover 12. In more specific terms, the indicator ring 40 will move or be forced, at least partially due to the influence of gravity thereon, from the "trapped" orientation of FIGS. 5 and 5A into the "captured" orientation, concurrent and/or subsequent to a snap-action detachment of the tip cap 20 from the indicator ring 40.

Yet additional features of this additional one or more preferred embodiments of the closure 10' include each of the first and second snap structures 22' in 24 having an angled segment 26 and integrally or fixedly formed thereon, so as to move therewith. The angled segments 26 and 28 of the first and second snap structures 22' in 24 of this additional embodiment can be structurally and/or operationally equivalent or at least similar to those described with the above-noted embodiment of the closure 10, as represented in FIGS. 1-3A. Therefore, the angled segments 26 and 28 of the first and second snap structures 22' and 24 respectively associated with the indicator ring 40 and the tip cap 20 are disposed in movable, sliding engagement with one another, concurrent to the exiting or removal of the tip cap 20 through the access opening 16, such as when the tip cap 20 is connected to a syringe or other appropriately configured medical container or device. Further, the indicator ring 40 has flexible construction. As with the cover 12 of the embodiment of FIGS. 1-3A, the flexible construction of the indicator ring 40 may be due to its formation from an at least partially flexible material and/or that the thickness of the sidewall 40' of the indicator ring 40 is sufficiently reduced to facilitate the outward flexure thereof, concurrent to the movable sliding engagement between the angled surfaces 26 and 28 of the first and second snap structures 22' in 24. This at least minimal outward flexure will facilitate the aforementioned movable sliding engagement and disconnection of the angled segments 26 and 28 of the first and second snap structures 22' in 24. In turn, at least a minimal outward flexure of the indicator ring will at least partially define a snap-action disconnection of said first and second snap structures 22' in 24 as well as a snap-action disconnection of the tip cap 20 from said indicator member or ring 40, when the indicator ring is in the aforementioned trapped orientation, as represented in FIGS. 5 and 5A.

However, one distinguishing structural feature of the at least one embodiment represented in FIGS. 4-6 from that represented in FIGS. 1-3A comprises an absence of the aforementioned stop segments 30 and 32 on the first and second snap structures 22' in 24. As a result, the tip cap 20 may be capable of being reinserted into the interior 14 of the cover 12. However, when the indicator ring 40 is disposed in the aforementioned "captured" orientation it will generally be disposed in supporting relation on the interior surface of the bottom or closed-end 18 of the cover 12. In turn, the second snap structure 24 disposed on the exterior surface 20' of the tip cap 20 will be sufficiently spaced from the indicator ring 40, even when the tip cap is fully re-inserted on the interior 14 of the cover 12 to prevent reattachment or engagement of the first and second snap structures 22' and 24. Therefore, the aforementioned tamper evident capabilities of this additional one or more embodiments of the closure 10'will be at least partially defined by a failure to retain the tip cap 20 within the cover 12 and/or establish a reconnection or attachment between the first and second snap structures 22' and 24 of the indicator ring 40 and the tip cap 20.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A tamper evident closure for a medical container comprising:
   a cover including an access opening and an oppositely disposed closed-end,
   a tip cap structured and configured to be attached to the medical container and removably disposed within said cover,
   a first snap structure disposed within said cover and a second snap structure disposed on said tip cap, initially within said cover,
   said first snap structure integrally and fixedly connected to an inner surface of said cover; said second snap structure integrally and fixedly connected to an outer surface of said tip cap,
   said first and second snap structures cooperatively disposed and configured to removably restrict exiting of said tip cap from said cover, via said access opening,
   each of said first and second snap structures including an angled segment disposed in sliding engagement with one another, concurrent to said exiting of said tip cap, via said access opening, and each of said first and second snap structures further including a stop segment disposable in abutting, insertion preventive engagement with one another, concurrent to reentry of said tip cap within said cover.

2. The tamper evident closure as recited in claim 1 wherein said cover is dimensioned and configured to define an outward flexure thereof, concurrent to said sliding engagement of said angled segments; said outward flexure defining a snap-action disconnection of said tip cap from said cover.

3. The tamper evident closure as recited in claim 1 wherein said angled segments of said first and second snap structures are respectively disposed at a substantially 120° angle relative to said inner surface of said cover and said outer surface of said tip cap.

4. The tamper evident closure as recited in claim 1 wherein said stop segment of each of said first and said second snap segments is respectively disposed in substantially perpendicular relation to said inner surface of said cover and said outer surface of said tip cap.

5. The tamper evident closure as recited in claim 1 wherein said first and second snap structures are fixedly connected to and movable with said cover and said tip cap respectively.

6. The tamper evident of closure as recited in claim 1 when at least one of said first and second snap structures comprises a substantially annular configuration.

7. The tamper evident closure as recited in claim 1 wherein said tip cap and said second snap structure are collectively dimensioned to pass through said access opening, concurrent to said exiting of said tip cap.

8. A tamper evident closure for a medical container comprising:

a cover including an access opening and an oppositely disposed closed-end, a tip cap structured and configured to be attached to the medical container and removably disposed within said cover, an indicator member movably disposed within said cover, initially in an exit restricting relation to said tip cap, a first snap structure integrally and fixedly connected to an inner surface of said indicator member; a second snap structure integrally connected to an outer surface of said tip cap, said exit restricting relation of said of said indicator member with said tip cap comprising said first and second snap structures disposed in removable, sliding engagement with one another, said indicator member movable within an interior of said cover from a trapped orientation into a captured orientation, subsequent to said removable, sliding engagement between said first and second snap structures and concurrent to said exiting of said tip cap via said access opening, and said captured orientation comprising said indicator member movably disposed within said interior of said cover, between said access opening and said closed-end.

9. The tamper evident closure as recited in claim 8 wherein said exit restricting relation further comprises said indicator member disposed in a trapped orientation between said tip cap and an interior surface of said cover.

10. The tamper evident closure as recited in claim 9 wherein said indicator member comprises an indicator ring initially disposed in surrounding relation to said tip cap and dimensioned to include an outer diameter greater than an inner diameter of said access opening.

11. The tamper evident closure as recited in claim 8 wherein said cover comprises a shelf structure disposed within said cover, said shelf structure having a smaller inner diameter than an outer diameter of the indicator member; said trapped orientation further comprising said indicator member disposed between said shelf structure and said tip cap, concurrent to said first and second snap structures disposed in said removable sliding engagement with one another.

12. The tamper evident closure as recited in claim 11 wherein said captured orientation further comprises said indicator member movably disposed within said cover, between said shelf and said closed-end.

13. The tamper evident closure as recited in claim 8 wherein each of said first and second snap structures include an angled segment, said angled segments disposed in removable and movable, sliding engagement with one another, concurrent to said exiting of said tip cap, via said access opening.

14. The tamper evident closure as recited in claim 13 wherein said indicator member is dimensioned and structured to define an outward flexure thereof, concurrent to said sliding engagement of said angled segments; said outward flexure defining a snap-action disconnection of said tip cap from said indicator member.

* * * * *